United States Patent [19]

Guttmann et al.

[11] 4,322,368

[45] Mar. 30, 1982

[54] COPPER-PROMOTED ANTIMONY PHOSPHATE OXIDE COMPLEX CATALYSTS

[75] Inventors: Andrew T. Guttmann, Maple Heights; Robert K. Grasselli, Chagrin Falls, both of Ohio

[73] Assignee: The Standard Oil Co., Cleveland, Ohio

[21] Appl. No.: 107,941

[22] Filed: Dec. 28, 1979

[51] Int. Cl.$^3$ ................. C07C 120/14; C07C 120/00; C07C 121/32
[52] U.S. Cl. ................. 260/465.3; 252/435; 252/437; 260/465.9; 568/477; 585/443; 585/628
[58] Field of Search ........................ 260/465.3, 465.9

[56] References Cited

U.S. PATENT DOCUMENTS

| | | | |
|---|---|---|---|
| 3,546,138 | 12/1970 | Callahan et al. | 252/456 |
| 3,892,794 | 7/1975 | Grasselli et al. | 260/465.3 |
| 3,956,181 | 5/1976 | Grasselli et al. | 260/465.3 X |
| 3,988,359 | 10/1976 | Saito et al. | 260/465.3 |
| 4,139,552 | 2/1979 | Grasselli et al. | 260/465.3 |
| 4,162,234 | 7/1979 | Grasselli et al. | 260/465.3 X |
| 4,174,354 | 11/1979 | Grasselli et al. | 260/465.3 X |

Primary Examiner—Joseph Paul Brust
Attorney, Agent, or Firm—John E. Miller, Jr.; Herbert D. Knudsen; Larry W. Evans

[57] ABSTRACT

Oxide complexes comprising copper-promoted antimony phosphates have been found to exhibit significant catalytic activity in various oxidation-type reactions such as the ammoxidation of propylene to produce acrylonitrile.

12 Claims, No Drawings

COPPER-PROMOTED ANTIMONY PHOSPHATE OXIDE COMPLEX CATALYSTS

BACKGROUND OF THE INVENTION

The present invention relates to new oxide complex catalysts for use in various oxidation-type reactions.

Oxide complexes of varying different compositions have been found to exhibit catalytic activity in different types of oxidation reactions, such as for example the oxidation of olefins to produce acids and aldehydes, the ammoxidation of olefins to produce unsaturated nitriles and the oxydehydrogenation of olefins to produce diolefins. As is known, such oxide complexes are relatively complex structures the exact nature of which is not understood. In operation, such catalysts continuously lose and gain oxygen and hence they are often referred to as redox catalysts.

It is an object of the present invention to provide a new type of oxide complex redox catalyst useful in a wide variety of different oxidation-type reactions.

SUMMARY OF THE INVENTION

This and other objects are accomplished by the present invention which is based on the discovery that copper-promoted antimony phosphate is an effective catalyst in various types of oxidation reactions and specifically the ammoxidation of propylene or isobutylene to produce acrylonitrile and methacrylonitrile, respectively.

Thus, the present invention provides novel catalysts for use in various types of oxidation-type reactions, the novel catalysts comprising oxide complex represented by the formula:

$$Sb_m Cu_n A_a C_e P_p D_d O_x$$

wherein

A is one or more elements selected from the alkali metals, alkaline earth metals and thallium;

C is one or more elements selected from the group consisting of Fe, Co, Ni, Mn, Cr, Bi, Zn, Cd and B;

D is one or more elements selected from the group consisting of As, Te, Ge, Sn, Ti and V;

and wherein m is 5–15;

n is 0.01–5;

a is 0–2;

e is 0–7.5;

p is 5–15;

d is 0–2; and x is determined by the nature and the oxidation state of the other elements.

DETAILED DESCRIPTION

The novel catalysts provided by the present invention can be described as oxide complexes conforming to the following general formula:

$$Sb_m Cu_n A_a C_e P_p D_d O_x$$

wherein

A is one or more elements selected from the alkali metals, alkaline earth metals and thallium;

C is one or more elements selected from the group consisting of Fe, Co, Ni, Mn, Cr, Bi, Zn, Cd and B;

D is one or more elements selected from the group consisting of As, Te, Ge, Sn, Ti and V;

and wherein m is 5–15;

n is 0.01–5;

a is 0–2;

e is 0–7.5;

p is 5–15;

d is 0–2; and x is determined by the nature and the oxidation state of the other elements.

In the preferred embodiment of the invention, a major portion (and preferably at least 80%) of the oxide complex exhibits the known layer structure as described, for example, in B. Kinberger, Act. Chem. Scand. 1970, 24 (1), 320-8 (Eng), CA 72, 115581u. Thus, preferably, the Sb/P ratio varies between 0.7/1 to 1/0.7, more preferably 0.8/1 to 1/0.8. Also, such catalysts further preferably contain tellurium in amounts such that d is 0.1 to 1. Furthermore, the catalysts are also preferably free of molybdenum since it has been found that the combination of molybdenum and copper in an antimony phosphate based catalyst adversely affects catalytic activity. Also, in the catalysts of the invention, and especially those in which the Sb/P ratio is between 0.7/1 to 1/0.7, preferably 0.8/1 to 1/0.8, it is preferred that the total number of atoms in the oxide complex other than Sb, P and O (i.e. Cu, A, C and D) be between 0.1 to 10, preferably 0.3 to 5, more preferably 1–3.5, based on the sum of the Sb and P atoms in the oxide complex being 20.

In these catalysts, antimony is normally present as trivalent antimony. However, it is also within the scope of the invention to formulate the catalysts in such a way that a portion of the antimony is present in pentavalent form. If the catalyst contains pentavalent antimony, the amount of pentavalent antimony is preferably less than the amount of trivalent antimony, more preferably 0.001 to 30% of the antimony content and even more preferably no more than about 10% of the total antimony content. In any case, at least 70% of the antimony in the catalyst must be present in the trivalent state. Preferably, oxide complex catalysts of the invention which contain elements other than copper, phosphorus, antimony and oxygen are free of pentavalent antimony.

The inventive oxide complex catalysts can be used either unsupported or supported on a suitable support. Any conventional support material such as silica, alumina, Alundum, zirconia, titania, graphite and so forth can be employed. Any amount of support material can also be employed with amounts of support between 5% and 95%, more preferably about 10% to 50% on a weight basis being preferred.

The catalysts of the present invention can be prepared using procedures adapted from the known synthesis of SbPO$_4$ from phosphoric acid and Sb$_2$O$_3$. See, for example, Robbins, J. Inorg. Nuclear Chem. 19, 183-5 (1961). Also see British Pat. No. 792,997. In such preparations, compounds containing the elements of the objective catalysts are dissolved in hot H$_3$PO$_4$, followed by the addition of silica, or other support, and Sb$_2$O$_3$. The mixture is then digested by heating with moderate heat for 30 minutes to 10 hours, dried, and then calcined in air or other oxygen-containing gas for 0.5 to 50 hours at 400° C. to 800° C. Most of the catalytic elements are supplied in the form of nitrates or acetates, while tellurium is normally supplied as TeO$_2$. If the objective catalyst is to contain pentavalent antimony, antimony pentachloride can be employed as the pentavalent antimony source, the antimony pentachloride being mixed with concentrated phosphoric acid prior to admixing with the other ingredients of the catalyst. Other compounds of pentavalent antimony, e.g. $Sb_2O_5$, can also be used.

The oxide complex catalysts of the present invention can be used in a wide variety of different oxidation-type reactions as described below.

Ammoxidation

A wide variety of different reactants can be ammoxidized in accordance with the present invention to produce nitriles. For example, olefins such as propylene and isobutylene, alcohols such as t-butyl alcohol, and aldehydes such as acrolein and methacrolein can be readily converted to nitriles in accordance with the present invention. In general, compounds which can be converted to nitriles by the inventive ammoxidation reaction include 3 to 9 carbon atom hydrocarbons unsubstituted or substituted with oxygen or hydroxy. Preferred starting materials are olefins, aldehydes and alcohols containing 3 or 4 carbon atoms.

The general ammoxidation process for converting olefins, alcohols and aldehydes to nitriles is well known. See, for example, U.S. Pat. No. 3,546,138, the disclosure of which is incorporated herein by reference. In general, the ammoxidation reaction is accomplished by contacting the reactant, oxygen and ammonia with a particular catalyst in the vapor phase. The inventive reaction is carried out in the same manner and under the conditions generally set forth in this patent.

In a preferred aspect the inventive process comprises contacting a mixture comprising propylene or isobutylene, ammonia and oxygen with the promoted catalyst of this invention at an elevated temperature and at atmospheric or near atmospheric pressure.

Any source of oxygen may be employed in this process. For economic reasons, however, it is preferred that air be employed as the source of oxygen. From a purely technical viewpoint, relatively pure molecular oxygen will give similar results. The molar ratio of oxygen to the olefin in the feed to the reaction vessel should be in the range of 0.5:1 to 4:1 and a ratio of about 1:1 to 3:1 is preferred.

Low molecular weight saturated hydrocarbons do not appear to influence the reaction to an appreciable degree, and these materials can be present; consequently, the addition of saturated hyrocarbons to the reaction feed is contemplated within the scope of this invention. Likewise, diluents, such as nitrogen and the oxides of carbon, may be present in the reaction mixture without deleterious effect.

The molar ratio of ammonia to olefin in the feed to the reactor may vary between about 0.05:1 to 5:1. There is no real upper limit for the ammonia/olefin ratio, but there is generally no reason to exceed the 5:1 ratio. At ammonia/olefin ratios appreciably less than the stoichiometric ratio of 1:1, various amounts of oxygenated derivatives of the olefin will be formed.

Significant amounts of unsaturated aldehydes, as well as nitriles, will be obtained at ammonia-olefin ratios substantially below 1:1, i.e., in the range of 0.15:1 to 0.75:1. Above the upper limit of this range, the amount of aldehydes produced rapidly decreases. It is fortuitous that within the ammonia-olefin range stated, maximum utilization of ammonia is obtained and this is highly desirable. It is generally possible to recycle any unreacted olefin and unconverted ammonia.

Water can also be included in the feed although it is not essential. In some instances, e.g. fixed-bed systems, water may improve the selectivity of the reaction and the yield of nitrile. However, reactions not including water in the feed are also within the scope of the present invention.

In general, the molar ratio of added water to olefin, when water is added, is in the neighborhood of 0.1:1 or higher. Ratios on the order of 1:1 to 3:1 are particularly desirable, but higher ratios may be employed, i.e. up to about 10:1.

The reaction is carried out at an elevated temperature such as 200° C. to 600° C., preferably 400° C. to 500° C. The pressure at which the reaction is conducted is also an important variable, and the reaction should be carried out at about atmospheric or slightly above atmospheric (2 to 3 atmospheres) pressure. In general, high pressures, i.e. above 15 atmospheres, are not suitable since higher pressures tend to favor the formation of undesirable byproducts.

The apparent contact time is not critical, and contact times in the range of from 0.1–50 seconds may be employed. The optimal contact time will, of course, vary depending upon the reactant being used, but in general, contact time of from 1–15 seconds is preferred.

The inventive ammoxidation reaction is carried out in the vapor phase. Normally, the process is conducted on a continuous basis using either a fixed-bed or a fluid-bed catalyst. However, a batch operation can be employed.

The reaction product passing out of the reactor is normally in the form of a gas. Conventionally, this gaseous reaction product is treated to remove $NH_3$ and then partially condensed either by indirect contact with a cooling medium or direct contact with water to form a liquid phase containing acrylonitrile, acrolein, acrylic acid, HCN and acetonitrile and a vapor phase containing $CO_2$, CO, $N_2$ and $O_2$. The acrylonitrile is then separated from the liquid phase by a number of different techniques such as, for example, distillation or water extraction/distillation. Additional steps can be employed to separately recover HCN and/or acetonitrile from the gross reaction product.

Oxidation

As previously indicated, the catalysts of this invention can also be employed in the catalytic oxidation of olefins to various different reaction products.

The reactants used in the oxidation to oxygenated compounds are oxygen and an olefin such as propylene, isobutylene and other olefins having up to three contiguous carbon atoms (i.e. three carbon atoms arranged in a straight chain).

The olefins may be in admixture with paraffinic hydrocarbons, such as ethane, propane, butane and pentane; for example, a propylene-propane mixture may constitute the feed. This makes it possible to use ordinary refinery streams without special preparation.

The temperature at which this oxidation is conducted may vary considerably depending upon the catalyst, the particular olefin being oxidized and the correlated conditions of the rate of throughput or contact time and the ratio of olefin to oxygen. In general, when operating at pressures near atmospheric, i.e. 0.1 to 10 atmospheres, temperatures in the range of 150° C. to 600° C. may be advantageously employed. However, the process may be conducted at other pressures, and in the case where superatmospheric pressures, e.g. above 10 atmospheres are employed, somewhat lower temperatures are possible. In the case where this process is employed to convert propylene to acrolein, a temperature range of 200° C. to 500° C. has been found to be optimum at atmospheric pressure.

While pressures other than atmospheric may be employed, it is generally preferred to operate at or near atmospheric pressure, since the reaction proceeds well at such pressures, the use of expensive high pressure equipment is avoided, and formation of undesired by-products and waste is diminished.

The apparent contact time employed in the process is not critical and it may be selected from a broad operable range which may vary from 0.1 to 50 seconds. The apparent contact time may be defined as the length of time in seconds which a unit volume of gas measured under the conditions of reaction is in contact with the apparent unit volume of the catalyst. It may be calculated, for example, from the apparent volume of the catalyst bed, the average temperature and pressure of the reactor, and the flow rates of the several components of the reaction mixture.

The optimum contact time will, of course, vary depending upon the olefin being treated, but in the case of propylene and isobutylene, the preferred contact time is 0.15 to 15 seconds.

A molar ratio of oxygen to olefin between about 0.5:1 to 5:1 generally gives the most satisfactory results. For the conversion of propylene to acrolein, a preferred ratio of oxygen to olefin is from about 1:1 to about 2.5:1. The oxygen used in the process may be derived from any source; however, air is the least expensive source of oxygen and is preferred for that reason.

The addition of water to the reaction mixture in oxidation reactions can have a beneficial influence on the conversion and yields of the desired product especially in fixed-bed reactions. The manner in which water affects the reaction is not fully understood. In any event, it is preferred in fixed-bed operation to include water in the reaction mixture, and in general a ratio of olefin to water in the reaction mixture of from 1:1.25 to 1:10 will give very satisfactory results while a ratio of 1:0.5 to 1:6 has been found the optimum when converting propylene to acrolein.

Inert diluents such as oxygen and carbon dioxide, may be present in the reaction mixture.

Oxydehydrogenation

In accordance with the present invention, the promoted catalyst system of the present invention can also be employed in the catalytic oxidative dehydrogenation of olefins to diolefins and aromatic compounds. In this process, the feed stream in vapor form containing the olefin to be dehydrogenated and oxygen is conducted over the promoted catalyst at a comparatively low temperature to obtain the corresponding diolefin.

By the term "olefin" as used herein is meant open chain as well as cyclic olefins. The olefins dehydrogenated in accordance with this invention have at least four and up to about nine nonquaternary carbon atoms, of which at least four are arranged in series in a straight chain or ring. The olefins preferably are either normal straight chain or tertiary olefins. Both cis and trans isomers, where they exist, can be dehydrogenated.

Among the many olefinic compounds which can be dehydrogenated in this way are butene-1; butene-2; pentene-1; pentene-2; pentenes, hexenes, etc. such as 2-methyl-pentene-1, 3-methylbutene-1, 3,4-dimethyl-pentene-1, 4-methyl-pentene-2; heptene-1; octene-1; cyclopentene; cyclohexene, 3-methyl cyclohexene and cycloheptene.

Open chain olefins yield diolefins, and, in general, six-membered ring olefins yield aromatic ring compounds. The higher molecular weight open chain olefins may cyclize to aromatic ring compounds.

The feed stock in addition to the olefin and oxygen can contain one or more paraffins or naphthenic hydrocarbons having up to about ten carbon atoms, which may be present as impurities in some petroleum hydrocarbon stocks and which may also be dehydrogenated in some cases.

The amount of oxygen can be within the range of from about 0.3 to about 4 moles per mole of double-bond created. Stoichiometrically, 0.5 mole of oxygen is required for the dehydrogenation of one mole of monolefin to a diolefin. It is preferred to employ an excess of oxygen, e.g. an oxygen/olefin ratio of from 0.6 to about 3, in order to ensure a higher yield of diolefin per pass. The oxygen can be supplied as pure or substantially pure oxygen or as air.

When pure oxygen is used, it may be desirable to incorporate a diluent in the mixture such as steam, carbon dioxide or nitrogen.

The feed stock can be catalytically dehydrogenated in the presence of steam, but this is not essential. When steam is used, from about 0.1 to about 6 moles of steam per mole of olefin reactant is employed, but amounts larger than this can be used.

The dehydrogenation proceeds at temperatures within the range of from about 300° C. to about 1,000° C. Optimum yields are obtainable at temperatures within the range from about 400° C. to 550° C.

The preferred reaction pressure is approximately atmospheric, within the range of from about 0.1 to about 5 atmospheres.

Only a brief contact time with the catalyst is required for effective dehydrogenation. The apparent contact time with the catalyst can vary from about 0.1 up to about 50 seconds but higher contact times can be used if desired. At these contact times, comparatively small reactors and small amounts of catalyst can be used effectively.

Process Conditions

In carrying out the foregoing processes, any apparatus of the type suitable for carrying out oxidation reactions in the vapor phase may be employed. The processes may be conducted either continuously or intermittently. The catalyst may be a fixed-bed employing a large particulate or pelleted catalyst or, in the alternative, a fluid-bed catalyst may be employed.

EXAMPLES

In order to more thoroughly describe the present invention, the following working examples are presented.

EXAMPLES 1 TO 85

In these examples, various catalysts were employed in the conventional ammoxidation reaction to convert propylene to acrylonitrile. In each example, 5 cc. of catalyst of 20 to 35 mesh was charged into a fixed-bed micro-reactor and contacted with a feed comprising 1.0 propylene/1.2 $NH_3$/2.0 $O_2$/3 $3H_2O$ at a reaction temperature of 420° C. for a contact time of 6 seconds. The oxygen was supplied as air. The gross reaction product was recovered and analyzed and the amounts of acrylonitrile and byproducts determined.

Each of the catalysts used in the examples was made by the general technique described above. A representative procedure to prepare the catalyst of Example 73 having the formula $Sb_{8.6}FeCu_{0.5}Te_{0.5}P_{9.6}O_x$ supported on 20% silica is given as follows.

A mixture of 2.75 gms. $Cu(NO_3)_2.3H_2O$ and 9.21 gms. $Fe(NO_3)_3.9H_2O$ was dissolved in 25.40 gms. 85% $H_3PO_4$ at 90° C. to 95° C. To this solution was added 1.82 gms. $TeO_2$, and the resulting mixture heated with stirring to 130° C. to 140° C. for 5 minutes. It was then cooled to 80° C., and 30.6 gms. 40% stabilized silica sol and 15 ml. water were added. Then 28.8 gms. $Sb_2O_3$ was stirred in rapidly followed by agitation at 60° C. to 65° C. The mixture set to a putty-like mass after 10 to 20 minutes. It was held in an oven at 65° C. for 6 hours, then dried overnight at 140° C. to 145° C., and further treated 20 hours at 350° C. The catalyst was then ground, screened and calcined at 525° C. for 5 hours.

Catalysts containing pentavalent antimony are made in essentially the same way as described above except that a compound of pentavalent antimony, e.g. $SbCl_5$, is added to the phosphoric acid prior to the addition of the other components. A representative procedure to prepare the catalyst of Example 9 having the formula $Sb_{9.3}CuP_9Sb^VO_x$ supported on 20% silica is given as follows.

Antimony pentachloride (9.04 gms.) was added dropwise, with agitation to 31.38 gms. 85% $H_3PI_4$, at 110° C. To the above mixture 7.30 gms. solid $Cu(NO_3)_2.3H_2O$ was added in small portions, during 30 minutes, at about 100° C. Initially forming precipitate was dissolved by adding 3 to 4 ml. of $H_2O$. The resulting blue viscous solutions was then heated for approximately 40 minutes until the temperature reached 135° C. to 140° C., and the evolution of nitrous fumes had almost ceased. The liquid was cooled to about 70° C., 42.3 gms. 40% stabilized silica sol was added, followed by addition of 41.14 gms. $Sb_2O_3$ at 60° C. to 65° C. The mixture set to a putty-like mass after 2 hours at 60° C. Subsequent procedure was identical to that given above for the catalyst of Example 73.

The compositions of the various catalysts, the final calcination temperature, the surface area of the catalyst and the results obtained are set forth in the following Tables I to VI. Unless otherwise indicated, all catalysts contain 20% silica and were subjected to the same heat treatment described above in connection with the preparation of the catalyst of Example 73 except that the final calcination temperature was as indicated.

TABLE I

SbPO$_4$-Based Catalysts - Propylene Ammoxidation
Effect of Heat Treatment and Pentavalent Antimony
Reaction Temp. 420° C.; CT = 6 sec.; $C_3/NH_3/O_2/H_2O$ = 1.0/1.2/2.0/3.3

| Example | Catalyst Composition | Heat Treatment (°C.) | Surface Area $m^2/g$ | % Propylene Conversion | % Yields AN | Aceto | HCN | $CO_x$ | % Select. AN |
|---|---|---|---|---|---|---|---|---|---|
| 1 | $Sb_{9.3}CuP_{10}O_x$ | 600 | 17.0 | 31.5 | 22.2 | 2.2 | 1.9 | 5.2 | 70.5 |
| 2 | " | 600 | | 33.3 | 23.7 | 2.1 | 1.6 | 5.9 | 71.0 |
| 3 | " | 675 | 14.9 | 27.7 | 20.1 | 1.9 | 2.1 | 3.6 | 72.6 |
| 4 | " | 750 | 10.2 | 19.4 | 14.1 | 1.0 | 1.5 | 1.4 | 72.6 |
| 5 | " | 750 | | 21.7 | 15.6 | 1.0 | 1.5 | 2.2 | 71.8 |
| 6 | $Sb_{9.3}CuP_{9.5}Sb_{0.5}{}^VO_x$ | 600 | | 53.1 | 26.7 | 1.6 | 2.9 | 20.9 | 50.3 |
| 8 | " | 750 | | 12.5 | 8.6 | 0.8 | 1.4 | 1.5 | 69.3 |
| 9 | $Sb_{9.3}CuP_9Sb^VO_x$ | 600 | 21.5 | 58.4 | 32.8 | 1.2 | 1.4 | 22.2 | 56.3 |
| 10 | " | 675 | 15.9 | 56.6 | 33.3 | 1.3 | 1.3 | 20.2 | 58.9 |
| 11 | " | 675 | | 53.9 | 33.5 | 1.0 | 1.6 | 17.9 | 62.0 |
| 12 | " | 750 | 11.1 | 16.6 | 13.2 | 0.9 | 1.3 | 1.3 | 79.2 |
| 13 | $Sb_{9.3}CuP_8Sb_2{}^VO_x$ | 600 | 21.7 | 8.1 | 5.6 | 1.0 | 0.8 | 0.7 | 79.2 |
| 14 | " | 600 | | 7.0 | 4.4 | 0.6 | 0.5 | 1.3 | 63.5 |
| 15 | " | 675 | 20.7 | 6.7 | 4.7 | 0.7 | 0.7 | 0.6 | 69.8 |
| 16 | " | 750 | 13.6 | 5.4 | 3.3 | 0.7 | 0.9 | 0.5 | 61.0 |
| 17 | " | 750 | | 4.4 | 2.9 | 0.6 | 0.9 | 0.0 | 65.0 |

From the foregoing Table I, it can be seen that copper-promoted antimony phosphate optionally containing pentavalent antimony is capable of providing significant yields of acrylonitrile in the conventional ammoxidation of propylene. Moreover, it will be seen that the yields of propylene obtainable can be affected by both the heat treatment to which the catalyst is subjected during preparation and the concentration of pentavalent antimony.

The following Examples 18 to 33 show the effect on AN yields obtainable by varying the copper content and the pentavalent antimony content in catalysts of the invention as well as the effect of the use of additional promoter elements.

TABLE II

SbPO$_4$-Based Catalysts - Propylene Ammoxidation
Variation of Copper and Sb$^V$; Additional Promoters
Reaction Temp. 420° C.; CT = 6 sec.; $C_3/NH_3/O_2/H_2O$ = 1.0/1.2/2.0/3.3

| Example | Catalyst Composition | Heat Treatment (°C.) | Surface Area $m^2/g$ | % Propylene Conversion | % Yields AN | Aceto | HCN | $CO_x$ | % Select. AN |
|---|---|---|---|---|---|---|---|---|---|
| 18 | $Sb_{8.7}Cu_2P_9Sb_2{}^VO_x$ | 600 | 20.4 | 32.8 | 20.1 | 0.4 | 1.3 | 11.0 | 61.2 |
| 19 | " | 675 | 18.0 | 40.3 | 25.4 | 1.1 | 3.0 | 10.6 | 63.0 |
| 20 | " | 750 | 12.4 | 12.9 | 9.3 | 0.7 | 1.3 | 1.5 | 72.4 |
| 21 | $Sb_{8.83}CuBi_{0.5}P_9Sb^VO_x$ | 600 | | 45.3 | 22.8 | 1.9 | 1.8 | 16.6 | 50.4 |
| 22 | " | 675 | | 33.2 | 20.9 | 1.4 | 2.9 | 7.8 | 63.0 |
| 23 | $Sb_{9.3}CuP_{10}O_x$ | 600 | 17.0 | 31.5 | 22.2 | 2.2 | 1.9 | 5.2 | 70.5 |
| 24 | $Sb_{9.3}CuAs_{0.5}P_{9.5}O_x$ | 600 | | 28.2 | 20.5 | 1.3 | 1.9 | 4.4 | 72.6 |

TABLE II-continued

SbPO$_4$-Based Catalysts - Propylene Ammoxidation
Variation of Copper and Sb$^V$; Additional Promoters
Reaction Temp. 420° C.; CT = 6 sec.; C$_3$/NH$_3$/O$_2$/H$_2$O = 1.0/1.2/2.0/3.3

| Example | Catalyst Composition | Heat Treatment (°C.) | Surface Area m$^2$/g | % Propylene Conversion | % Yields AN | Aceto | HCN | CO$_x$ | % Select. AN |
|---|---|---|---|---|---|---|---|---|---|
| 25 | Sb$_{9.3}$CuTe$_{0.5}$P$_{9.6}$O$_x$ | 600 | 22.3 | 76.0 | 49.8 | 3.1 | 0.5 | 22.5 | 65.5 |
| 26 | Sb$_{8.6}$Cu$_2$P$_{10}$O$_x$ | 600 | 23.3 | 41.5 | 26.8 | 1.6 | 2.3 | 10.8 | 64.5 |
| 27 | Sb$_{8.6}$Cu$_2$As$_{0.5}$P$_{9.5}$O$_x$ | 600 | | 38.7 | 28.9 | 0.9 | 1.7 | 7.2 | 74.7 |
| 28 | Sb$_{8.6}$Cu$_2$Te$_{0.5}$P$_{9.6}$O$_x$ | 600 | 24.8 | 62.1 | 34.2 | 1.3 | 0.0 | 26.5 | 55.1 |
| 29 | Sb$_{9.6}$Cu$_{0.5}$Te$_{0.5}$P$_{8.6}$Sb$^V$O$_x$ | 525 | | 42.9 | 30.4 | 1.2 | 2.2 | 9.0 | 71.0 |
| 30 | " | 600 | | 50.1 | 35.3 | 1.0 | 1.8 | 11.7 | 70.5 |

Examples 18 to 30 also show that copper-promoted antimony phosphates when containing pentavalent antimony as well as when containing other promoting elements provide significant yields of acrylonitrile in the conventional ammoxidation reaction.

The following Examples 31 to 48 in Table III show the effect and advantages of including tellurium in the copper-promoted antimony phosphates of the present invention.

TABLE III

SbPO$_4$-Based Catalysts Containing Copper and Tellurium - C$_3$ Ammoxidation
Effect of Cu and Te Concentration and of Heat Treatment
Reaction Temp. 420° C.; CT = 6 sec.; C$_3$/NH$_3$/O$_2$/H$_2$O = 1.0/1.2/2.0/3.3

| Example | Catalyst Composition | Heat Treatment (°C.) | Surface Area m$^2$/g | % Propylene Conversion | % Yields AN | Aceto | HCN | CO$_x$ | % Select. AN |
|---|---|---|---|---|---|---|---|---|---|
| 31 | Sb$_{9.3}$CuTe$_{0.1}$P$_{9.93}$O$_x$ | 525 | | 69.9 | 42.0 | 13.4 | 0.0 | 13.3 | 60.0 |
| 32 | " | 600 | | 73.2 | 40.8 | 11.4 | 2.2 | 16.6 | 55.7 |
| 33 | " | 675 | | 65.8 | 42.8 | 9.6 | 3.4 | 9.7 | 65.1 |
| 34 | Sb$_{9.3}$CuTe$_{0.5}$P$_{9.6}$O$_x$ | 525 | 34.1 | 78.5 | 46.6 | 5.2 | 0.8 | 25.7 | 59.4 |
| 35 | " | 600 | 27.6 | 80.0 | 46.5 | 8.4 | 1.7 | 22.3 | 58.2 |
| 36 | " | 675 | 17.8 | 58.2 | 38.7 | 6.8 | 2.0 | 10.2 | 66.5 |
| 37 | Sb$_{9.3}$CuTeP$_{9.3}$O$_x$ | 525 | | 66.6 | 40.7 | 6.3 | 0.9 | 18.2 | 61.1 |
| 38 | " | 600 | | 59.7 | 36.8 | 8.2 | 1.4 | 11.7 | 61.7 |
| 39 | " | 675 | | 48.6 | 33.9 | 5.8 | 2.0 | 6.5 | 69.7 |
| 40 | Sb$_{9.6}$Cu$_{0.5}$Te$_{0.5}$P$_{9.6}$O$_x$ | 525 | | 81.4 | 46.4 | 9.2 | 1.3 | 24.0 | 57.0 |
| 41 | " | 600 | | 77.9 | 48.6 | 7.1 | 2.1 | 20.0 | 62.4 |
| 42 | " | 675 | | 61.4 | 42.3 | 7.6 | 2.6 | 8.1 | 68.9 |
| 43 | Sb$_{9.86}$Cu$_{0.2}$Te$_{0.1}$P$_{9.93}$O$_x$ | 525 | | 60.9 | 38.9 | 9.6 | 3.2 | 8.8 | 63.9 |
| 44 | " | 600 | | 64.8 | 41.1 | 9.4 | 3.2 | 10.8 | 63.5 |
| 45 | " | 675 | | 67.8 | 41.7 | 10.3 | 2.9 | 12.6 | 61.4 |
| 46 | Sb$_{9.86}$Cu$_{0.2}$TeP$_{9.33}$O$_x$ | 525 | | 62.5 | 41.0 | 7.3 | 2.0 | 11.2 | 65.7 |
| 47 | " | 600 | | 49.1 | 30.8 | 8.9 | 1.6 | 7.0 | 62.7 |
| 48 | " | 675 | | 43.6 | 29.5 | 6.8 | 1.5 | 5.8 | 67.6 |

Table III shows that catalysts containing tellurium as well as copper provide excellent yields of acrylonitrile in the conventional ammoxidation reaction.

The following Examples 49 to 71 as set forth in Table IV show the effect of additional promoters on copper-promoted antimony phosphates also containing tellurium.

TABLE IV

SbPO$_4$-Based Catalysts Containing Copper and Tellurium - C$_3$ Ammoxidation
Effect of Additional Promoters
Reaction Temp. 420° C.; CT = 6 sec.; C$_3$/NH$_3$/O$_2$/H$_2$O = 1.0/1.2/2.0/3.3

| Example | Catalyst Composition | Heat Treatment (° C.) | Surface Area m$^2$/g | % Propylene Conversion | % Yields AN | Aceto | HCN | CO$_x$ | % Select. AN |
|---|---|---|---|---|---|---|---|---|---|
| 49 | K$_{0.1}$Sb$_{9.3}$CuTe$_{0.5}$P$_{9.6}$O$_x$ | 600 | 23.0 | 61.6 | 40.1 | 3.2 | 1.5 | 17.4 | 65.0 |
| 50 | " | 525 | 32.3 | 74.6 | 47.9 | 2.8 | 1.1 | 22.3 | 64.1 |
| 51 | Tl$_{0.1}$Sb$_{9.3}$CuTe$_{0.5}$P$_{9.6}$O$_x$ | 525 | | 63.6 | 39.2 | 6.3 | 2.2 | 15.9 | 61.7 |
| 52 | Cs$_{0.1}$Sb$_{9.3}$CuTe$_{0.5}$P$_{9.6}$O$_x$ | 525 | | 59.4 | 37.9 | 4.2 | 1.9 | 14.9 | 63.8 |
| 53 | Cs$_{0.05}$Sb$_{9.3}$CuTe$_{0.5}$P$_{9.6}$O$_x$ | 525 | | 57.8 | 31.4 | 5.7 | 0.9 | 19.5 | 54.2 |
| 54 | Cs$_{0.05}$Sb$_8$Cu$_2$Te$_{0.5}$P$_{9.6}$O$_x$ | 525 | | 65.9 | 32.9 | 4.9 | 0.3 | 27.2 | 50.0 |
| 55 | Li$_{0.2}$Sb$_{9.6}$Cu$_{0.5}$Te$_{0.5}$P$_{9.6}$O$_x$ | 525 | | 63.8 | 46.3 | 2.1 | 2.0 | 13.2 | 72.5 |
| 56 | Mg$_{0.2}$Sb$_{9.1}$CuTe$_{0.5}$P$_{9.6}$O$_x$ | 525 | | 70.4 | 41.4 | 7.0 | 1.6 | 20.0 | 58.8 |
| 57 | " | 600 | | 64.8 | 39.5 | 6.4 | 2.1 | 16.3 | 61.0 |
| 58 | Ca$_{0.5}$Sb$_9$CuTe$_{0.5}$P$_{9.6}$O$_x$ | 525 | | 82.9 | 50.4 | 8.1 | 0.6 | 23.7 | 60.8 |
| 59 | K$_{0.1}$Ca$_{0.45}$Sb$_{9.6}$CuTe$_{0.5}$P$_{9.6}$O$_x$ | 525 | | 72.9 | 46.8 | 8.5 | 2.0 | 15.6 | 64.2 |
| 60 | La$_{0.5}$Sb$_{8.8}$CuTe$_{0.5}$P$_{9.6}$O$_x$ | 525 | | 81.7 | 39.0 | 11.8 | 0.6 | 30.2 | 47.8 |
| 61 | ZrSb$_8$CuTe$_{0.5}$P$_{9.6}$O$_x$ | 525 | | 82.2 | 43.3 | 9.5 | 0.0 | 29.4 | 52.6 |
| 62 | Sb$_9$Ce$_{0.3}$CuTe$_{0.5}$P$_{9.6}$O$_x$ | 525 | | 78.3 | 35.8 | 10.7 | 0.0 | 31.5 | 45.7 |
| 63 | " | 600 | | 83.6 | 41.8 | 9.2 | 0.0 | 32.1 | 50.0 |
| 64 | Sb$_{9.3}$CuTe$_{0.5}$As$_{0.3}$P$_{9.4}$O$_x$ | 600 | | 66.6 | 39.9 | 9.8 | 1.7 | 14.2 | 59.9 |

TABLE IV-continued

SbPO₄-Based Catalysts Containing Copper and Tellurium - C₃ Ammoxidation
Effect of Additional Promoters
Reaction Temp. 420° C.; CT = 6 sec.; $C_3/NH_3/O_2/H_2O = 1.0/1.2/2.0/3.3$

| Example | Catalyst Composition | Heat Treatment (°C.) | Surface Area m²/g | % Propylene Conversion | % Yields AN | Aceto | HCN | $CO_x$ | % Select. AN |
|---|---|---|---|---|---|---|---|---|---|
| 65 | $Sb_9Bi_{0.3}CuTe_{0.5}P_{9.6}O_x$ | 600 | | 83.5 | 46.0 | 11.1 | 1.3 | 24.2 | 55.1 |
| 66 | $Sb_{8.9}Ge_{0.3}CuTe_{0.5}P_{9.6}O_x$ | 600 | | 88.3 | 49.4 | 10.4 | 0.6 | 27.7 | 56.0 |
| 67 | $Sb_{8.9}Sn_{0.3}CuTe_{0.5}P_{9.6}O_x$ | 525 | | 81.8 | 39.6 | 12.0 | 0.8 | 29.0 | 48.5 |
| 68 | " | 600 | | 88.0 | 45.1 | 13.7 | 0.9 | 27.6 | 51.2 |
| 69 | $Sb_{9.3}CuTe_{0.5}W_{0.3}P_{9.5}O_x$ | 600 | | 27.2 | 14.4 | 7.3 | 2.0 | 3.0 | 53.1 |
| 70 | $Sb_{9.6}Cu_{0.5}Te_{0.5}Mo_{0.3}P_{9.5}O_x$ | 525 | | 62.2 | 28.1 | 4.6 | 0.0 | 15.0 | 45.3 |
| 71 | $Sb_{8.7}Co_{0.6}Fe_{0.2}CuTe_{0.5}P_{9.6}O_x$ | 525 | 24.5 | 90.4 | 49.2 | 13.3 | 1.3 | 25.6 | 54.4 |

As noted from Table IV, copper-promoted antimony phosphates also containing tellurium can also contain many additional elements as promoters.

Examples 72 to 85 in the following Table V show the effects of cobalt and iron as promoters on copper-promoted antimony phosphates also containing tellurium.

their performance in the oxidation of propylene to produce acrolein and acrylic acid. In these reactions, 5 cc. of catalyst having a mesh size of 20 to 35 mesh were charged into a 5 cc. continuous flow micro-reactor and contacted with a feed comprising 1 propylene/2.3 oxygen/4.0 H₂O at 380° C. for a contact time of 3 seconds.

TABLE V

SbPO₄-Based Catalysts Containing Copper and Tellurium - C₃ Ammoxidation
Effect of Cobalt and Iron
Reaction Temp. 420° C.; CT = 6 sec.; $C_3/NH_3/O_2/H_2O = 1.0/1.2/2.0/3.3$

| Example | Catalyst Composition | Heat Treatment (°C.) | Surface Area m²/g | % Propylene Conversion | % Yields AN | Aceto | HCN | $CO_x$ | % Select. AN |
|---|---|---|---|---|---|---|---|---|---|
| 72 | $Sb_{8.7}CuCo_{0.6}Fe_{0.2}P_{10}O_x$ | 600 | | 34.2 | 18.7 | 7.4 | 3.1 | 4.6 | 54.7 |
| 73 | $Sb_{8.6}FeCu_{0.5}Te_{0.5}P_{9.6}O_x$ | 525 | 34.9 | 82.3 | 55.1 | 4.9 | 2.6 | 19.0 | 67.0 |
| 74 | $Sb_{8.7}Fe_{0.9}Co_{0.1}Cu_{0.5}Te_{0.5}P_{9.6}O_x$ | 525 | | 75.9 | 50.4 | 4.6 | 2.8 | 17.5 | 66.5 |
| 75 | $Sb_{8.6}Fe_{0.6}Co_{0.6}Cu_{0.5}Te_{0.5}P_{9.6}O_x$ | 525 | 30.6 | 82.4 | 58.4 | 5.9 | 2.5 | 15.4 | 70.8 |
| 76 | $Sb_{8.6}Fe_{0.6}Co_{0.6}Cu_{0.5}Te_{0.5}P_{9.6}O_x$ | 600 | | 63.0 | 46.3 | 3.4 | 3.5 | 9.4 | 73.5 |
| 77 | $Sb_{8.8}Fe_{0.5}Co_{0.5}Cu_{0.5}Te_{0.5}P_{9.6}O_x$ | 525 | 34.5 | 82.4 | 56.1 | 5.8 | 2.8 | 16.9 | 68.1 |
| 78 | $Sb_{8.7}Fe_{0.2}Co_{0.6}CuTe_{0.5}P_{9.6}O_x$ | 600 | 24.5 | 76.2 | 48.5 | 11.0 | 3.2 | 13.2 | 63.7 |
| 79 | $Sb_{8.7}Fe_{0.2}Co_{0.6}CuTe_{0.5}P_{9.6}O_x$ | 675 | | 49.9 | 32.9 | 7.3 | 2.8 | 6.3 | 66.0 |
| 80 | $Sb_{8.8}Fe_{0.2}CoCu_{0.5}Te_{0.5}P_{9.6}O_x$ | 525 | | 81.5 | 54.1 | 6.8 | 1.3 | 19.2 | 66.4 |
| 81 | $Sb_{8.8}Fe_{0.2}CoCu_{0.5}Te_{0.5}P_{9.6}O_x$ | 600 | | 61.7 | 46.1 | 3.2 | 2.6 | 9.6 | 74.7 |
| 82 | $Sb_9Fe_{0.1}Co_{0.9}Cu_{0.5}Te_{0.5}P_{9.6}O_x$ | 525 | | 78.5 | 45.3 | 7.8 | 1.0 | 24.1 | 57.8 |
| 83 | $Sb_9CoCu_{0.5}Te_{0.5}P_{9.6}O_x$ | 525 | | 81.6 | 46.2 | 8.1 | 1.1 | 25.5 | 56.6 |
| 84 | $Li_{0.1}Sb_{8.6}Co_{0.6}Fe_{0.6}Cu_{0.5}Te_{0.5}P_{9.6}O_x$ | 525 | | 81.6 | 55.2 | 5.5 | 3.6 | 16.2 | 67.7 |
| 85 | $Sb_{8.8}Fe_{0.5}Co_{0.5}Cu_{0.5}Te_{0.5}P_{8.6}Sb^VO_x$ | 525 | | 25.0 | 19.5 | 0.9 | 2.1 | 2.6 | 77.8 |

As can be seen, cobalt and iron provide significant promoting effects in copper-promoted antimony phosphates also containing tellurium.

EXAMPLES 86 TO 88

Copper-promoted antimony phosphates in accordance with the present invention were also tested for The oxygen was supplied as air. The final calcination temperature of the catalyst, the surface area of the catalyst, the composition of the catalyst and the results obtained are set forth in the following Table VI.

TABLE VI

SbPO₄-Based Catalysts Containing Cu and Other Elements - C₃ Oxidation
Reaction Temp. 380° C.; CT = 3 sec.; $C_3/O_2/H_2O = 1.0/2.3/4.0$

| Example | Catalyst Composition | Heat Treat (°C.) | Surface Area m²/g | % Propylene Conversion | % Yields Acrolein | Acrylic Acid | Acetone | Acet Ald | Acet Acid | $CO_x$ | % Select* |
|---|---|---|---|---|---|---|---|---|---|---|---|
| 86 | $Sb_{9.5}Cu_{0.75}P_{10}O_x$ | 550 | 21.4 | 9.5 | 6.71 | 0.2 | 0.0 | 0.8 | 0.2 | 1.6 | 72.9 |
| 87 | $Sb_{9.5}Cu_{0.6}Ru_{0.1}P_{10}O_x$ | 550 | 12.9 | 16.5 | 4.00 | 0.5 | 0.5 | 4.5 | 1.0 | 6.5 | 26.5 |
| 88 | $Sb_{9.3}CuP_9Sb^VO_x$ | 610 | 12.9 | 9.9 | 6.90 | 0.2 | 0.0 | 0.4 | 0.1 | 2.3 | 71.3 |

*Acrolein and Acrylic Acid

From the foregoing, it can be seen that the inventive catalysts also provide significant activity in the known oxidation reaction for converting propylene to acrolein and acrylic acid.

Although only a few embodiments of the present invention have been described above, it should be appreciated that many modifications can be made without departing from the spirit and scope of the invention. All such modifications are intended to be included within the scope of the present invention, which is to be limited only by the following claims:

We claim:

1. In an ammoxidation process for producing a nitrile in which a reactant selected from the group consisting of propylene, isobutylene, t-butyl alcohol, acrolein and methacrolein together with oxygen and ammonia in the vapor phase are contacted with an oxide complex catalyst at elevated temperature, the improvement wherein said catalyst is an antimony phosphate having an Sb/P ratio of 0.7/1 to 1/0.7, a majority of said catalyst having the SbPO$_4$ layered structure, at least 70% of the antimony in said oxide complex catalyst being in the trivalent state, said oxide complex catalyst consisting essentially of the formula $$Sb_m Cu_n A_a C_e P_p D_d O_x$$

wherein

A is one or more elements selected from the alkali metals, alkaline earth metals and thallium;

C is one or more elements selected from the group consisting of Fe, Co, Ni, Mn, Cr, Bi, Zn, Cd and B;

D is one or more elements selected from the group consisting of As, Te, Ge, Sn, and Ti;

and wherein m is 5–15;
n is 0.01–5
a is 0–2
e is 0–7.5
p is 5–15;
d is 0–1;
n+a+e+d=0.1 to 10 based on m+p=20; and
x is determined by the nature and the oxidation state of the other elements.

2. The process of claim 1 wherein said reactant is propylene and/or isobutylene.

3. The process of claim 2 wherein at least 80% of said catalyst has said layered structure, the Sb/P ratio in said catalyst is 0.8/1 to 1/0.8 and at least 90% of the Sb in said catalyst is in the trivalent state.

4. The process of claim 1 wherein said catalyst is free of molybdenum.

5. The process of claim 4 wherein said catalyst contains tellurium.

6. The process of claim 5 wherein said catalyst contains 0.1 to 1 atoms of tellurium based on the number of atoms in said formula.

7. The process of claim 1 wherein said catalyst is free of pentavalent antimony.

8. The process of claim 1 wherein n+a+e+d=0.35 to 5.

9. The process of claim 8 wherein n+a+e+d=1 to 3.5.

10. The process of claim 1 wherein said catalyst contains pentavalent antimony.

11. The process of claim 1 wherein said catalyst contains 0 to 1 atoms Fe based on 9.6 atoms P.

12. The process of claim 11 wherein said catalyst contains Fe.

* * * * *